United States Patent [19]
Contant-Pussard et al.

[11] Patent Number: 6,020,150

[45] Date of Patent: *Feb. 1, 2000

[54] GELLED SYSTEM AND METHOD FOR DETECTING MICROORGANISMS BY SEPARATION AND CULTURE ON GELLED SYSTEM

[75] Inventors: Geneviève Contant-Pussard, Courbevoie; Françoise Boisard-Beaupere, Paris; Jean-Luc Martinoli, Villeneuve la Garenne; Alain Rousseau, Paris, all of France

[73] Assignee: Diffusion Bacteriologie Du Var, France

[*] Notice: This patent issued on a continued prosecution application filed under 37 CFR 1.53(d), and is subject to the twenty year patent term provisions of 35 U.S.C. 154(a)(2).

[21] Appl. No.: 08/913,757

[22] PCT Filed: Mar. 20, 1996

[86] PCT No.: PCT/FR96/00419

§ 371 Date: Sep. 22, 1997

§ 102(e) Date: Sep. 22, 1997

[87] PCT Pub. No.: WO96/29427

PCT Pub. Date: Sep. 26, 1996

[30] Foreign Application Priority Data

Mar. 20, 1995 [FR] France ..................... 95 03214

[51] Int. Cl.$^7$ .............. C12Q 1/04; C12Q 1/06; C12Q 1/08; C12N 1/02
[52] U.S. Cl. ............... 435/34; 435/39; 435/40; 435/261
[58] Field of Search ............... 435/34, 39, 40, 435/261

[56] References Cited

U.S. PATENT DOCUMENTS

| | | | |
|---|---|---|---|
| 3,932,222 | 1/1976 | Dorn | 195/127 |
| 4,131,512 | 12/1978 | Dorn | 195/103.5 M |
| 4,164,449 | 8/1979 | Dorn et al. | 435/30 |
| 4,190,328 | 2/1980 | Levine et al. | 350/320 |
| 4,212,948 | 7/1980 | Dorn | 435/296 |
| 4,717,660 | 1/1988 | Schulte | 435/30 |

FOREIGN PATENT DOCUMENTS

| | | |
|---|---|---|
| 0 454 509 | 10/1991 | European Pat. Off. . |
| 0 496 409 | 7/1992 | European Pat. Off. . |
| 2 577 321 | 8/1986 | France . |
| WO 91/04318 | 4/1991 | WIPO . |

OTHER PUBLICATIONS

Dorn et al., "Blood Culture Technique Based on Centrifygation : Developmental Phase", Journal of Clinical Microbiology, Mar. 1976, vol. 3, No. 3, pp. 251–257.

*Primary Examiner*—Sandra E. Saucier
*Assistant Examiner*—Vera Afremova
*Attorney, Agent, or Firm*—Evenson, McKeown, Edwards & Lenahan, P.L.L.C.

[57] ABSTRACT

A method for detecting the presence or absence of microorganisms belonging to the group which consists of bacteria and yeasts in a liquid sample (5) of a biological material. The method comprises placing the liquid sample (5) in a centrifuge tube (6a, 6b) above a gelled system (10) comprising at least (a) a first so-called development phase (1), i.e. a gel comprising a microorganism culture medium and a reagent for inducing a detectable optical measurement change in the presence of microorganisms, said gel being an intimate mixture of water and water-absorbing polymeric particles that have swelled in such a way that, in said intimate mixture, said polymeric particles have ($\alpha$) a dry weight concentration of 0.05–0.2 g/ml, and ($\beta$) a swollen-state diameter of 90–320 $\mu$m, the water in the intimate mixture being at least partially provided by said culture medium; centrifuging; and revealing the presence or absence of microorganisms in said liquid sample (5) at said first phase (1) of the gelled system (10) by means of said reagent inducing a detectable optical measurement change.

31 Claims, 3 Drawing Sheets

GELLED SYSTEM AND METHOD FOR DETECTING MICROORGANISMS BY SEPARATION AND CULTURE ON GELLED SYSTEM

FIELD OF THE INVENTION

The present invention relates to a novel method of detecting the presence or absence of microorganisms belonging to the group comprising bacteria and yeasts. This method uses a technique involving separation, culture and development on one and the same gelled system.

It further relates on the one hand to said gelled system as a novel industrial product, and on the other hand to the assay kit for carrying out said method.

Finally, it relates to the use of said method and said gelled system in microbiology (especially in bacteriology or mycology), particularly in the field of the detection of bacterial infections (more particularly the detection of urinary infections and septicemia).

PRIOR ART

When it is desired to assess the presence or absence of microorganisms such as bacteria and yeasts, especially by a colorimetric method, the following results have to be considered:

true positives (TP), false positives (FP), true negatives (TN) and false negatives (FN).

In practical terms, the following four values (expressed as percentages) have been defined from the TP, FP, TN and FN results which are theoretically possible:

the sensitivity (Sen), the specificity (Spe), the positive predictive value (PPV) and the negative predictive value (NPV), said values being such that:

Sen=100. TP/(TP+FN),

Spe=100. TN/(TN+FP),

PPV=100. TP/(TP+FP) and

NPV=100.TN/(TN+FN), in order to evaluate the significance or the pertinence of the measurements.

It is known on the one hand that a colorimetric detection or filtration technique has already been recommended or used for assessing the presence or absence of bacteria in urine, and on the other hand that a gel separation technique has already been recommended or used for revealing erythrocyte agglutinates.

As far as colorimetric detection is concerned, the publication EP-A-0 496 409 has disclosed a method of revealing Gram-negative bacteria. This method comprises the filtration of a biological sample (especially urine) containing bacteria on a porous support (pore diameter 0.75–1.2 $\mu$m) in order to retain the bacteria on said support, and then the detection of the Gram-negative bacteria by reaction of their dehydrogenases with a redox color reagent (especially a tetrazolium salt or resazurin), the reduction reactions induced by the Gram-positive bacteria being inhibited by means of a caotropic agent and a non-ionic detergent of the alkylglucoside type.

As far as the colorimetric filtration technique is concerned, tests marketed by VITEK SYSTEMS (Haziewood, Mo.) under the names "Bac-T-Screen®" (semi-automatic test) and "FiltraCheck®-UTI" (manual test) are known in particular.

These tests are performed by filtering a urine sample on a filter paper impregnated with a developer in order to retain and color the bacteria which may be present in the sample; the filtration is carried out under a pressure difference, so a relatively complicated apparatus is required; the main source of errors (FP and FN results) is due to the possible presence of a large number of erythrocytes, leukocytes and/or epithelial cells in the urine (the presence of erythrocytes and/or leukocytes in the urine is already in itself a sign of dysfunction).

According to the literature—cf. (a) page 272 (Table 3) and page 274 (section "Colorimetric Filtration") of the article by M. PEZZLO, *Clin. Microbiol. Rev.*, 1988, 1 (No. 2), 268–280, and (b) page 86 (paragraph "Systeme coloration filtration" ("Coloration/filtration system") and Tables) of the article by F. W. GOLDSTEIN, *Méd. Mal. Infect.*, 1991, 21, 83–88—the Bac-T-Screene® and FiltraCheck®-UTI tests are (i) rapid (1–2 minutes), (ii) effective when the bacterial population is $\geq 10^5$ CFU/ml, but (iii) unsatisfactory when said bacterial population is below $10^5$ CFU/ml. Overall, taking these two tests together, the two articles cited above give the following results for urine screenings according to the bacterial populations:

$\geq 10^5$ CFU/ml: Sen=93–95%, Spe=76–77%, PPV=32% and NPV=97–99%;

$\geq 10^4$ CFU/ml: Sen=85–89%, Spe=81% and NPV=84–86%; and $\geq 10^3$ CFU/ml: Sen=76–84% and NPV=67–72%.

There is therefore a need to improve the reliability of the measurements for bacterial populations below $10^5$ CFU/ml.

As far as the gel separation technique for assessing erythrocyte agglutination is concerned, the publications FR-A-2 577 321 and EP-A-0 454 509 are known.

According to FR-A-2 577 321, the formation or presence of erythrocyte agglutinates is revealed by (1) the deposition of a liquid medium containing erythrocytes on a gel which (i) is located in a conical-bottomed centrifuge tube and (ii) allows the free corpuscles to pass through more easily than the agglutinates [especially a gel marketed under the name "Sephadex® G 100 Ultrafine" by PHARMACIA FINE CHEMICALS (Uppsala, Sweden)], and then (2) gentle centrifugation.

The procedure according to EP-A-0 454 509 is substantially analogous and involves gentle centrifugation, the gel of FR-A-2 577 321 being replaced with a gelled system consisting of a mixture of two dextran gels (cf. especially page 3 lines 2–4 and page 4 lines 6–7 of EP-A-0 454 509), namely the product "Sephadex® G 100 Ultrafine" mentioned above, which, in the dry state, is in the form of particles with a diameter of 20 to 50 $\mu$m, and the product "Sephadex® HP Ultrafine", which, in the dry state, is in the form of particles with a diameter of 13 to 23 $\mu$m.

According to the information provided in EP-A-0 454 509 (page 3 lines 2–4 and 42–43 and page 4 lines 14–15), it seems clear that the gelled system of EP-A-0 454 509 contains only one phase.

As described in FR-A-2 577 321 and EP-A-0 454 509, the gel separation technique with centrifugation is not directly applicable to the detection of the presence or absence of microorganisms. In particular, the gels recommended, namely the products "Sephadex® G 100 Ultrafine" and "Sephadex® HP Ultrafine", do not allow the passage of microorganisms such as bacteria and yeasts during the gentle centrifugation [i.e. according to the prior art: an intensity less than or equal to 1500 g, in particular an intensity less than 1000 g (especially of the order of 400–500 g, EP-A-0 454 509 indicating, on page 4 line 49, an intensity of 430 g)], nor the separation of bacteria from the other cells.

OBJECT OF THE INVENTION

According to the invention, it is proposed to provide a novel technical solution for detecting, in a sample of a biological material, the presence or absence of microorganisms belonging to the group comprising bacteria and yeasts, this novel technical solution giving more reliable results for microbial populations below $10^5$ germs/ml (hereafter, for the sake of convenience, 1 bacterium/ml or 1 yeast/ml will be considered to correspond approximately to 1 CFU/ml) than the above-mentioned "Bac-T-Screen®" and "TiltraCheck®-UTI" tests relating to the evaluation of bacterial urinary infections.

This novel technical solution uses a particular technique for the separation of microorganisms on a gelled system containing a culture medium which is different from the technique proposed by the publications FR-A-2 577 321 and EP-A-0 454 509 cited above, and which avoids isolation of the microorganisms on a standard agar system or the cultivation necessary for their multiplication, prior to centrifugation.

SUBJECT OF THE INVENTION

This object is achieved by the use of a gelled system which on the one hand selectively separates the microorganisms which may be present in a sample of a biological material from the other components, especially the cells, the peptides and the proteins, and which on the other hand allows said microorganisms to grow in situ during the centrifugation and then, if appropriate, after said centrifugation and their development.

According to a first feature of the invention, a novel method is recommended for detecting the presence or absence of microorganisms belonging to the group comprising bacteria and yeasts in a liquid sample of a biological material which may contain cells other than those of said microorganisms, said method, which uses a gel separation technique, being characterized in that it comprises the steps consisting in:
(1°) using a gelled system which (i) separates, according to their size, the microorganisms which may be present in said liquid sample, and which originate from said biological material, from the other solid components which may be present in said liquid sample, (ii) is essentially impermeable to the water which may be present in said liquid sample and to the dissolved substances which may be present in said liquid sample, and (iii) comprises at least
   (a) a first, so-called development phase which is a gel containing a microorganism culture medium and a reagent which induces a detectable variation in optical measurement in the presence of microorganisms, said gel being an intimate mixture of water and water-absorbing polymer particles which have been swollen so that, in said intimate mixture, said polymer particles have a concentration by dry weight of between 0.05 and 0.2 g/ml and a diameter in the swollen state of between 90 and 320 μm, the water of said intimate mixture originating wholly or partly from said culture medium;
(2°) introducing said liquid sample into a centrifuge tube on top of said gelled system, which has been placed in said centrifuge tube beforehand;
(3°) centrifuging the resulting contents of said tube; and
(4°) revealing the presence or absence of microorganisms in said liquid sample originating from said biological material, in said first phase of the gelled system, by means of said reagent which induces a detectable variation in optical measurement.

If the concentration of the microorganisms in said liquid sample is too low, the development of step (4°) is carried out after multiplication of the microorganisms in said culture medium at a temperature between room temperature and 45° C., in at most 24 h (preferably in 1–2 h) in the case of bacteria and in at most 36 h (preferably in 24–30 h) in the case of yeasts.

According to a second feature of the invention, said gelled system which (i) separates, according to their size, the microorganisms which may be present in said liquid sample, and which originate from said biological material, from the other solid components which may be present in said liquid sample, (ii) is essentially impermeable to the water which may be present in said liquid sample, and (iii) comprises at least
   (a) a first, so-called development phase which is a gel containing a microorganism culture medium and a reagent which induces a detectable variation in optical measurement in the presence of microorganisms, said gel being an intimate mixture of water and water-absorbing polymer particles which have been swollen so that, in said intimate mixture, said polymer particles have a concentration by dry weight of between 0.05 and 0.2 g/ml and a diameter in the swollen state of between 90 and 320 μm, the water of said intimate mixture originating wholly or partly from said culture medium,
is recommended as a novel industrial product.

According to yet another feature of the invention, an assay kit is recommended which comprises in particular:
   said gelled system or the phases which make it up, and
   if appropriate, lyophilized reference strains of microorganisms and/or their culture media to allow the preparation of standard samples.

Finally, according to another feature of the invention, the use of said method and said gelled system is recommended in microbiology, especially in (i) the detection of bacterial infections (particularly such as urinary infections and septicemia), (ii) the identification of strains of microorganisms, and (iii) the evaluation of the antibiotic resistance of strains of microorganisms.

BRIEF DESCRIPTION OF THE DRAWINGS

The attached drawings schematically show centrifuge tubes each packed with a gelled system according to the invention.

ABBREVIATIONS

For the sake of convenience, the following abbreviations and acronyms have been used in the text of the present invention:

| | |
|---|---|
| Ala | alanyl |
| TB | tetrazolium blue |
| CFU | colony forming unit |
| DIC | disseminated intravascular coagulation |
| EDTA | ethylenediaminotetraacetic acid |
| FN | false negatives |
| FP | false positives |
| Hyp | hydroxyprolyl; Hyp represents 3Hyp (3-hydroxyprolyl) and/or 4Hyp (4-hydroxyprolyl) |
| INT | iodonitrotetrazolium |
| Leu | leucyl |
| Lys | lysyl |
| MA | 4-methylcoumarinyl-7-amino |
| MUG | 4-methylumbelliferyl-β-D-glucoronide |
| MW | molecular weight |
| NA | β-naphthylamino |
| NADH | hydrogenated nicotinamide adenine dinucleotide |
| TNB | tetrazolium nitroblue |
| NPV | negative predictive value |
| NTC | neotetrazolium chloride |
| OM | optical measurement |
| Phe | α-phenylalanyl |
| Phg | α-phenylglycyl |
| pNA | p-nitroanilino |
| PPV | positive predictive value |
| Pro | prolyl |
| RT | room temperature (15–20° C.) |
| Sen | sensitivity |
| Spe | specificity |
| TN | true negatives |
| TP | true positives |
| TTC | triphenyltetrazolium chloride |
| YNB | nitrogen source marketed under the tradename "YEAST NITROGEN BASE" |

DETAILED DESCRIPTION OF THE INVENTION

"Biological material" is understood here as meaning:

an aqueous human or animal body fluid, especially urine, blood, plasma, cerebrospinal fluid, pleural fluid, milk;

any type of water, especially running water (springs, rivers), stagnant water (ponds, reservoirs, swimming pools), industrial water (tap water, sewage water, circulating water functioning in particular as heat transfer fluid or energy transfer fluid, waste water), drinking water;

a drink, especially originating from agri-foodstuffs and based on water, such as fruit juices, fizzy drinks, milk (mentioned above), wine, beer;

a food of animal and/or vegetable origin or a food preparation;

a plant extract, especially an aqueous, alcoholic or aqueous-alcoholic extract, particularly a pressed-out juice or an aqueous extract;

a solid or viscous product such as, in particular, pus, biopsies, feces, sputum, saliva, a plant, part of a plant, soil, sand; said product may or may not contain water in its composition; and man's enviromnent in general (especially soil and water (mentioned above) on the one hand and the ambient atmosphere on the other); examples are given below for evaluation of the bacteriological and mycological quality of the atmosphere in operating theater suites.

In brief, said biological material will be selected from the group comprising body fluids, foods, drinks and the products of the environment (including plants and their extracts).

In practice it is recommended, but not essential, that said biological material be an aqueous product; for optimal implementation of the detection method of the invention, it suffices for said biological material to be converted (especially by grinding, dilaceration, extraction and/or addition of water) to a liquid sample, or already to be in liquid form, in order to be tested. Said liquid sample will advantageously be an aqueous liquid sample.

"Cell" is understood here as meaning any biological cell which is neither a bacterium nor a yeast. "Cellular material" is understood here as meaning a material selected from (i) cells, (ii) fragments of said cells (especially cell wall fragments), (iii) the content of said cells which belongs inside the wall, and (iv) mixtures thereof.

The biological material according to the invention in which it is desired to determine the presence or absence of microorganisms, and its liquid sample, can contain a cellular material.

By way of information, a patient's urine can contain on the one hand:

(A) in the case of a urinary infection, microorganisms such as:

Gram-negative bacteria, especially *Escherichia coli*, Klebsiella (in particular *Klebsiella aerogenes, Klebsiella pneumoniae*), Proteus (in particular *Proteus vulgaris, Proteus mirabilis*), Pseudomonas (in particular *Pseudomonas aeruginosa*), Serratia (in particular *Serratia marcescens*) and/or Enterobacter (in particular *Enterobacter aerogenes*), Gram-positive bacteria, especially Staphylococcus (in particular *Staphylococcus aureus, Staphylococcus epidermidis, Staphylococcus saprophyticus*), Streptococcus (in particular *Streptococcus faecalis, Streptococcus faecium*), Enterococcus and/or Corynebacterium, and/or yeasts, especially *Candida albicans, Candida glabrata* (former name: *Torulopsis glabrata*), *Candida tropicalis* and/or *Candida krusei*, which may be pathogenic (these strains can induce septicemia and DIC); and on the other hand:

(B) a cellular material comprising cells (in particular erythrocytes, leukocytes and/or epithelial cells), cellular enzymes (in particular urinary urokinase, leukocyte esterase and/or phosphatase), antibiotics (capable of interfering with or falsifying the detection of the microorganisms present in the urine), peptides, proteins, pigments and/or cell wall fragments.

According to the invention, on the one hand the undissolved particles of the liquid sample of said biological material will be caused to migrate through the gelled system so as to separate the microorganisms, according to their size, from the other undissolved solid components originating from said biological material, by centrifugation, and on the other hand said microorganisms will generally be grown in situ so that they can be detected.

"Reagent which induces a detectable variation in optical measurement" (alternative name: "colorimetric reagent") is understood here as meaning a product which, in the presence of a microorganism belonging to the group comprising bacteria and yeasts, causes a variation in OM which is assessed either with the naked eye or by means of a colorimeter. In other words, the reagent which changes color in the presence of microorganisms induces a color change in the visible spectrum or a change in fluorescence or luminescence, especially in the UV region.

Such a "colorimetric reagent" can be (i) a pH color indicator such as phenol red, (ii) a redox color indicator such as, in particular, dichloroindophenol, resazurin or a tetrazolium salt (for example TB, INT, TNB, NTC or TTC), (iii) a chromogenic substrate such as H-L-Ala-pNA, H-L-Leu-pNA, H-L-Phe-pNA, H-L-Pro-pNA, H-L-Lys-pNA or H-L-Hyp-pNA, or a fluorogenic substrate such as H-L-Ala-NA, H-L-Leu-NA, H-L-Phe-NA, H-L-Pro-NA, H-L-Lys-NA, H-L-Hyp-NA, H-L-Ala-MA, H-L-Leu-MA, H-L-Phe-MA, H-L-Pro-MA, H-L-Lys-MA, H-L-Hyp-MA or MUG phosphate, (iv) a substrate cleavable by an osidase of the microorganisms, such as β-D-glucosidase or, preferably, β-D-galactosidase, or (v) a chemoluminescent substrate such as a luciferin compound.

The redox color indicators are mainly oxidizing compounds which reveal the presence of microorganisms by reaction with at least one reducing substance originating from said microorganisms, such as, in particular, NADH and dehydrogenases. The mechanism is analogous to that illustrated below for resazunn:

resazurin+NADH→resorufin+NAD⁺

The chromogenic and fluorogenic substrates which are preferred according to the invention, namely H-L-Ala-pNA, H-L-Leu-pNA, H-L-Phe-pNA, H-L-Pro-pNA, H-L-Lys-pNA, H-L-Hyp-pNA, H-L-Ala-NA, H-L-Leu-NA, H-L-Phe-NA, H-L-Pro-NA, H-L-Lys-NA and H-L-Hyp-NA, are cleaved by the aminopeptidases produced by the microorganisms. Other peptide substrates cleavable by said aminopeptidases, which are described in published PCT application WO-A-90/03726, can also be used in the present invention.

As indicated above, the gelled system according to the invention, which is involved in step (1°) of the recommended method, comprises at least one gelled layer, namely the "development phase", also designated here by "first phase" or "first layer" for the sake of convenience. The development phase consists of a polymeric substance (especially of the dextran or analogous type) swollen beforehand with water so as to form a gel which retains in its bulk (or on its lower face in the case of the largest particles), during centrifugation, the insoluble particles contained in said liquid sample which have a size of between 0.5 and 8 μm.

It is important that, in the swollen state, said polymeric substance of the development phase has a concentration by dry weight of 0.05 to 0.2 g/ml (preferably a concentration of 0.1 g/ml) and is present (in the gel) in the form of swollen particles with a diameter of 90 to 320 μm, so that it retains in its bulk, or in the vicinity of its lower face, the bacteria (length: 0.5 to 5 μm; diameter: 0.1 to 2 μm) and the majority of the yeasts (diameter: 5 to 12 μm) but not the cells.

In practical terms, the polymeric substance of the development phase will be swollen beforehand with the culture medium for growing the microorganisms, said culture medium containing the above-mentioned colorimetric reagent which induces a variation in OM.

For carrying out step (1°) of the recommended method, the gelled system according to the invention can also comprise:

(b) a second, so-called absorption phase which is essentially impermeable to the water which may be present in said liquid sample and to the substances dissolved therein, which retains in its bulk the insoluble particles contained in said liquid sample which have a size less than 5 μm, but lets through the particles with a size greater than or equal to 5 μm, during centrifugation, and which consists of (i) a gel or (ii) silica or silicate particles with a size less than 0.1 μm, said second phase resting on said first phase, said intimate mixture being essentially impermeable to the water which may be present in said liquid sample.

In one modified embodiment, the "absorption phase", "second phase" or "second layer" is a gel consisting of an intimate mixture of water and water-absorbing polymer particles which have been swollen so that, in said intimate mixture, said polymer particles have (α) a concentration by dry weight of between 0.2 and 1 g/ml and (β) a diameter in the swollen state of between 160 and 530 μm,.

In this case the absorption phase consists of a polymeric substance (especially of the dextran or analogous type) swollen beforehand with water so as to form a gel, like said first phase, but so as to retain in its bulk (or on its lower face in the case of the largest particles), during centrifugation, on the one hand the insoluble particles contained in said liquid sample which have a smaller size of between 0.1 and 0.5 μm, and on the other hand the insoluble particles which do not pass through said first phase (i.e. with a size less than 5 μm).

In another modified embodiment, the absorption phase is a particulate layer consisting of a mineral substance which on the one hand is micronized so as to have a particle size less than 0.1 μm in the dry state, and on the other hand does not essentially swell in the presence of water. This mineral substance will advantageously be selected from the group comprising silica (especially sand, quartz or glass) and silicates such as aluminosilicates. Kaolin, a clay which does not swell in the presence of water, is more particularly recommended among the silicates.

It has in fact been found that mineral substances such as silica and kaolin with a particle size less than 0.1 μm let the microorganisms through and retain the water and the dissolved substances which may be present in said liquid sample.

Thus the absorption phase will prevent the passage of the undissolved solid particles of said liquid sample such as the hemoglobin, the pigments (especially the urinary pigments when it is desired to detect the presence or absence of microorganisms in the urine in the case of a urinary infection), the enzymes and the inhibitors, and will retain the undissolved particles such as the fragments of lyzed cells. By way of example, these fragments are retained after treatment with a lytic agent or in the presence of a lytic agent. This lytic agent can be a detergent, such as saponin, for lyzing the erythrocytes.

It is important that (1) in the swollen state, said polymeric substance of the absorption phase has a concentration by dry weight of 0.2 to 1 g/ml (preferably a concentration of 0.35 g/ml) and is present (in the gel) in the form of swollen particles with a diameter of 160 to 530 μm, and that (2) the mineral particles, such as micronized silica and kaolin, have a homogeneous diameter.

When it is present in said gelled system, said second phase advantageously contains one or more substances which inhibit any contaminants or lyze the cells (especially the erythrocytes and/or the leukocytes) and/or eliminate the lipids (as in the clarification of milk samples to be tested) which are contained in said liquid sample originating from said biological material and may interfere in step (4°) by reacting with said reagent which induces a detectable variation in optical measurement in the presence of microorganisms.

When said second phase is not present in the gelled system of the invention, it is recommended that said substance or substances (which inhibit, lyze and/or eliminate) be included in said first phase.

For carrying out step (1°) of the recommended method, the gelled system according to the invention can also comprise:

(c) a third, so-called barrier phase which cannot be crossed, during the centrifugation of step (3°), by any microorganisms present, said third phase being located underneath the first phase so that said first phase rests on said third phase.

Said third phase (or "third layer") is either a paraffin or a gel of a polymeric substance. When it is a paraffin, this is a solid paraffin which melts at a temperature above the multiplication temperature of the microorganisms, for example:

a paraffin melting at a temperature above or equal to 30° C., when the microorganism growth culture involved in step (4°) is carried out at RT, a paraffin melting at a temperature above or equal to 45° C., when the microorganism growth culture involved in step (4°) is carried out at 37° C., or a paraffin melting at a temperature above or equal to 50–55° C., when the microorganism growth culture involved in step (4°) is carried out at 45° C.

It will be preferable to use a paraffin melting at a temperature above or equal to 50° C., which will be introduced into the centrifuge tube in the molten state.

When the barrier phase is a gel, said gel will consist of an intimate mixture of water and water-absorbing polymer particles which have been swollen so that, in said intimate mixture, said polymer particles have ($\alpha$) a concentration by dry weight of between 0.04 and 0.2 g/ml and ($\alpha$) a diameter in the swollen state of between 30 and 130 $\mu$m.

Said gel consists of a polymeric substance (especially of the dextran or analogous type) swollen beforehand with water so as to form a gel, like said first phase, but so as to retain in its bulk or on its upper face, during centrifugation, the insoluble particles contained in said liquid sample which have a larger size (i.e. a size greater than or equal to 5 or 8 $\mu$m).

Thus the barrier phase will retain on its upper surface (in the case of solid paraffin) or in its bulk (in the case of gel) the cells, especially the erythrocytes with a mean size of 5–8 $\mu$m, the leukocytes with a mean size of 10–12 $\mu$m, the epithelial cells (in particular in the case of urine) with a mean size of 20–50 $\mu$m, the casts with a mean size greater than 40 $\mu$m, the crystals with a mean size of 20–200 $\mu$m, and the cell wall fragments (especially when the cells have been lyzed in their passage, during centrifugation, through the first phase or the combined second phase/first phase).

In practical terms, whatever the nature of the barrier phase, the solid particles contained in said liquid sample will spread out according to a gradient, with the smallest (i.e. the lightest) on top of the largest (i.e. the heaviest).

When the gelled system does not comprise the barrier phase, it is important that said gelled system be placed in a centrifuge tube with a conical bottom (as envisaged in the documents FR-A-2 577 321 and EP-A-0 454 509 cited above) or a bottom provided with a capillary. In this case, the heaviest solid particles spread out at the bottom of the centrifuge tube, as indicated above, with the microorganisms just above the cells.

It is important that, in the swollen state, said polymeric substance of the gel of the barrier phase has a concentration by dry weight of 0.04 to 0.2 g/ml (preferably a concentration of 0.14 g/ml) and is present in the form of swollen particles with a diameter of 30 to 130 $\mu$m.

When the barrier phase is present in the gelled system according to the invention, said gelled system can be accommodated in any type of centrifuge tube, especially a tube with a round or spherical bottom.

The presence of the absorption phase is advantageous in that it makes it possible to prevent the liquid (mainly the water) of said liquid sample from coming into contact with the development phase before and after centrifuigation.

The simultaneous presence of the absorption phase and the barrier phase is advantageous in that it enables a development phase of small thickness to be used. Consequently, the microorganisms present in the bulk or on the lower face of said development phase will be more concentrated in a given volume and hence more readily detectable during the colorimetric development (either with the naked eye or by means of a colorimeter).

The gelled system according to the invention which comprises said first phase, either on its own or associated with at least one of said second and third phases, is impermeable to the liquid of said liquid sample. During centrifugation, said liquid and the ingredients dissolved therein do not pass through said gelled system; on the other hand, the undissolved ingredients of said liquid sample migrate into the thickness of said gelled system and are separated according to their size, as explained above.

For carrying out step (1°) of the recommended method, the gelled system according to the invention can also comprise:

(d) a fourth, so-called protection phase which (i) is an inert oil with a density less than that of water, preferably a paraffin oil, (ii) before centrifugation, rests on said first phase in the absence of the second phase, or rests on said second phase when the latter is present in said gelled system, and (iii) after centrifugation according to step (3°), rests on the water of said liquid sample.

The oil of the protection phase has to be inert towards the constituents of the gelled system and the components of the liquid sample. An oil which melts at a temperature below RT and has a boiling point above 50° C., or even above 55° C., is more particularly recommended. A paraffin oil is particularly suitable. In practical terms, a volume of 0.25 to 1 ml of the protection phase will be introduced into a 5 ml centrifuge tube.

According to the invention, the protection phase advantageously serves two purposes: on the one hand it prevents dehydration and contamination of the gelled system during storage, and on the other hand it means that the layer of said gelled system on which it rests is not degraded when said liquid sample is poured into the centrifuge tube.

It is preferentially recommended to use in step (1°) either a gelled system comprising, from top to bottom, in a conical-bottomed centrifuge tube:

said fourth phase, said second phase and said first phase, or a gelled system comprising, from top to bottom, in a round-bottomed or spherical-bottomed centrifuge tube:

said fourth phase, said second phase, said first phase and said third phase, or a gelled system comprising, from top to bottom, in a capillary-bottomed centrifuge tube:

if appropriate, said fourth phase and/or said second phase, and in the capillary, said first phase.

The centrifugation of step (3°) is carried out above 500 g and in the range 1000 g to 5000 g (i.e. approximately at an angular velocity of 2200 to 4500 rpm when using the customary centrifugation devices). The duration of this centrifugation is at least 5 minutes and preferably 10 to 30 minutes. The centrifugation according to the invention will advantageously be carried out at 2000–4000 g for 15 minutes.

Said centrifugation according to the invention is generally carried out at RT. If required, said centrifugation can be carried out at a temperature between RT and 45° C. (preferably between RT and 37° C.), i.e. at a temperature analogous to that of the culture envisaged in step (4°) for growing the microorganisms which may be present in said liquid sample, but it is not essential to use a temperature above RT during the centrifugation.

When the protection phase is present in the gelled system of the invention, the liquid of said liquid sample migrates through said protection phase during the centrifugation; after said centrifugation, said liquid, devoid of the undissolved solid constituents which have also migrated, is situated between said protection phase and the absorption phase (if the latter is present) or the development phase (in the absence of the absorption phase in said gelled system).

The development envisaged in step (4°) takes place on the one hand during centrifugation and on the other hand, if appropriate, after culture of the microorganisms at a temperature between RT and 45° C. The duration of the culture required for growing the microorganisms generally depends on the initial concentration of said microorganisms (bacteria and/or yeasts) in said liquid sample.

In practice, for a liquid sample with an initial bacteria concentration below the detection threshold (i.e. $10^3$ germs/ml), it is necessary to anticipate a culture time of at most 24 h (preferably 1–2 h), except in the case of *Staphylococcus aureus* strains, which multiply relatively slowly (for said Staphylococcus strains, a culture time of about 24 h must be expected).

For a liquid sample with an initial yeast concentration below the detection threshold (i.e. $10^3$ germs/ml), it is necessary to anticipate a culture time of at most 36 h (preferably 24–30 h). To favor the detection of said yeasts, it is recommended to incorporate an antibacterial agent, such as that described in the document WO-A-90/03726 cited above, especially gentamycin, into the absorption phase and/or the development phase in order to inhibit bacterial growth or destroy said bacteria.

The culture medium used to swell the development phase comprises a carbon source, a nitrogen source and trace elements, for example a peptone (5 to 20 g/l), a sugar (1 to 20 g/l, preferably 5 g/l), a yeast extract (1 to 5 g/l) and vitamins (10 to 20 ml), with a buffer for stabilizing the pH at a value of between 6.0 and 8.0. For bacteria, this medium consists for example of a heart-brain broth with a sugar added. For yeasts, this medium can be either identical to that for bacteria, or different, for example a YNB+glucose medium, a Sabouraud medium or a YNB+maltose medium (which are described in WO-A-90/03726 cited above).

For Gram-negative bacteria, the culture medium used will advantageously be heart-brain broth+sugar containing the following as the preferred reagent which induces a detectable variation in optical measurement:

resazurin at a final concentration of 0.05 g/ml (0.2 mM), phenol red at a final concentration of about 0.065 g/ml (0.17 mM), the chromogenic substrate H-L-Ala-pNA at a final concentration of about 0.50 g/l (2 mM), or the fluorogenic substrate H-L-Ala-NA (about 2 mM), this medium being buffered at pH 6.5–8.0 by means of a phosphate or Tris buffer (0.1 M) and it being possible for this medium to contain the following if appropriate:

an activator belonging to the group comprising divalent cations, especially $Mg^{2+}$, $Ca^{2+}$ or $Mn^{2+}$ (for example a solution of $MnCl_2$ or $MnSO_4$ at about 30 mg/l), a diazotization reagent such as p-dimethylaminocinnamaldehyde or Fast Blue BB, and/or one or more inhibitors of the secondary reactions associated especially with the presence of enzymes in said liquid sample to be tested (for example, in the case of urine screening, aprotinin to inhibit the urinary urokinase and EDTA to inhibit the phosphatases).

In practice, the inhibitor or inhibitors can be placed in the development phase and/or the absorption phase.

For Gram-positive bacteria, the culture medium used will advantageously be the medium described above for Gram-negative bacteria, with the following as the preferred reagent which induces a detectable variation in optical measurement:

resazurin at a final concentration of about 0.05 g/ml, the chromogenic substrate H-L-Leu-pNA at a final concentration of about 2 mM, or the fluorogenic substrate H-L-Leu-NA at a final concentration of 2 mM, the pH being buffered at 6.0–8.0 and it being possible for said medium to contain, if appropriate, an activator, a diazotization reagent and/or one or more inhibitors, as indicated above.

For yeasts, the culture medium used will advantageously be a YNB+sugar medium buffered at pH 6.5–8.0, with the following as the preferred reagent which induces a detectable variation in optical measurement: the chromogenic substrate H-L-Pro-pNA or an equivalent substrate, an essential inhibitor being an antibiotic, such as gentamycin, streptomycin or chloramphenicol, for inhibiting bacterial growth. Said essential inhibitor can also be present in the absorption phase.

Other advantages and characteristics of the invention will be understood more clearly from the following description of the drawings and Examples. Of course, these data as a whole in no way imply a limitation, but are given by way of illustration.

The gelled system 10 according to the invention is accommodated in a centrifuge tube with a conical bottom, 6a, a spherical bottom, 6b, or a bottom provided with a capillary, 6c. Said gelled system 10 comprises at least one layer, namely the development phase 1, which is a gel swollen beforehand by means of an aqueous microorganism culture medium, and, if appropriate, one or more other layers, namely the absorption phase 2, which is either a gel swollen beforehand with water and capable of containing one or more inhibitors (such as aprotinin and EDTA), or a micronized particulate layer (silica or kaolin) with a particle size less than 0.1 μm, the barrier phase 3, which is a gel swollen beforehand with water or a layer of paraffin that is solid under the centrifugation and culture conditions, and/or the protection phase 4, which is a layer of paraffin that is liquid under said conditions.

Figure 1:
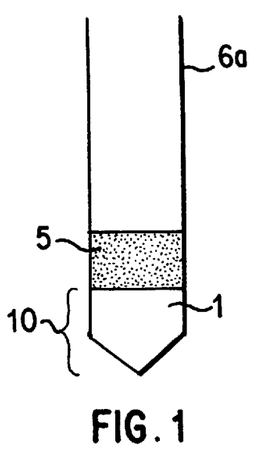
FIG. 1 shows a centrifuge tube containing a gelled system consisting of a single phase, namely the so-called development phase.

FIG. 1 relates to a gelled system 10 according to the invention comprising a single layer, the development phase 1, accommodated in a conical-bottomed centrifuge tube 6a. The liquid sample 5 is poured on top of said development phase 1. On centrifugation, the undissolved particles of said liquid sample migrate into the thickness of the development phase; on the other hand, the liquid of said liquid sample 5 and the dissolved ingredients do not pass through the development phase. After said centrifugation, the largest particles, which are the heaviest, are spread out at the bottom of the tube 6a according to their size, with the cells at the bottom and, above said cells, the microorganisms, which are located in the vicinity of the lower part of the development phase 1.

The gelled system according to FIG. 1 gives good results, but it is not totally satisfactory in that the gel of the development phase 1 (i) is in contact with said liquid sample 5 during centrifugation and culture, and (ii) can consequently be diluted by said liquid sample 5.

Figure 2A:
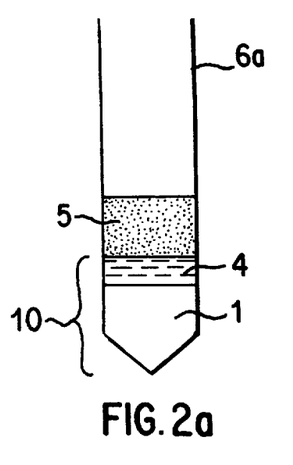
FIGS. 2a and 2b show a centrifuge tube containing a gelled system consisting of two phases, namely, from bottom to top, the development phase and the protection phase, as it appears before centrifugation (FIG. 2a) and after centrifugation (FIG. 2b)
Figure 2B:
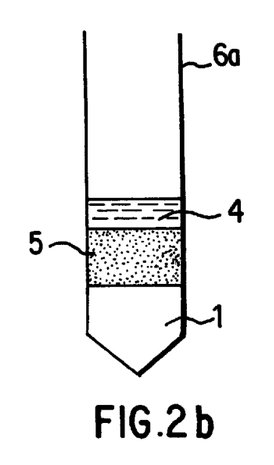

FIGS. 2a and 2b relate to the same gelled system 10 before centrifugation (FIG. 2a) and after centrifugation (FIG. 2b). Compared with the gelled system of FIG. 1, the gelled system of FIGS. 2a and 2b also comprises a layer of oil (liquid paraffin) constituting the protection phase. The development phase 1 is poured into the tube 6a, followed by the protection phase 4, and said gelled system 10 is compressed by centrifugation (2000–3000 g for 10–20 minutes). The liquid sample 5 to be tested is then poured into the tube 6a. Said liquid sample 5 spreads out on top of the protection phase 4 (cf FIG. 2a) before centrifugation.

During centrifugation, said liquid sample 5 migrates through the protection phase 4 together with the soluble ingredients it contains. Its solid particles migrate through the development phase 1, the heaviest of said particles spreading out at the bottom of the tube as indicated above for FIG. 1. After centrifugation, the liquid of the liquid sample 5 is located between the protection phase 4 and the development phase 1 (cf. FIG. 2b).

Although the gelled system of FIGS. 2a and 2b is admittedly better than that of FIG. 1, it nevertheless has the disadvantage that the liquid sample 5 is in contact with the development phase 1 after centrifugation during the so-called culture step.

Figure 3:
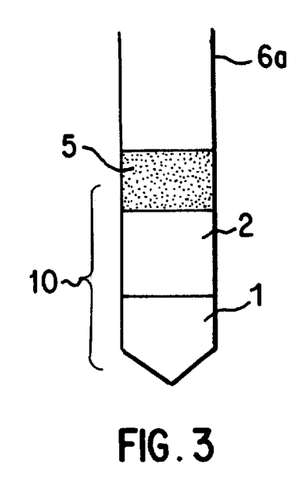
FIG. 3 shows a centrifuge tube containing a gelled system consisting of two phases, namely, from bottom to top, the development phase and the absorption phase.

FIG. 3 relates to a gelled system 10 according to the invention comprising two layers: the development phase 1 and the absorption phase 2. The development phase 1 is poured into the conical-bottomed centrifuge tube 6a, followed by the absorption phase 2, and said gelled system 10 is compressed by centrifugation (1000–3000 g for 10–20 minutes). The liquid sample 5 to be tested is then poured into the tube 6a. Said liquid sample 5 spreads out on top of the absorption phase.

During the centrifugation of step (3°), the solid particles contained in the liquid sample 5 migrate through the absorption phase 2 and/or the development phase 1 according to their size; on the other hand, the liquid of said liquid sample 5 and the ingredients dissolved therein do not pass through the absorption phase 2.

After the centrifugation of step (3°), the largest and heaviest particles of said liquid sample 5 are found at the bottom of the tube 6a, spread out as indicated above for FIGS. 1 and 2a–2b.

It is advantageous on the one hand that the development phase 1 is isolated from the liquid of said liquid sample 5 by the absorption phase 2 after the centrifugation of step (3°), and on the other hand that the absorption phase 2 absorbs the small particles.

Figure 4A:
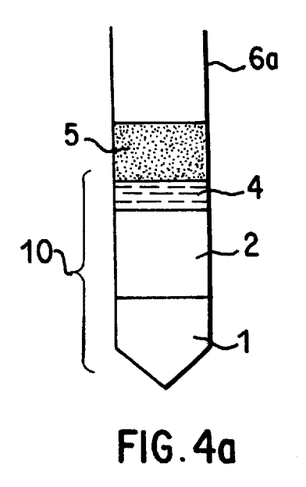
FIGS. 4a and 4b show a gelled system analogous to that of FIG. 3 which also contains the protection phase, as it appears before centrifugation (FIG. 4a) and after centrifugation (FIG. 4b)
Figure 4B:
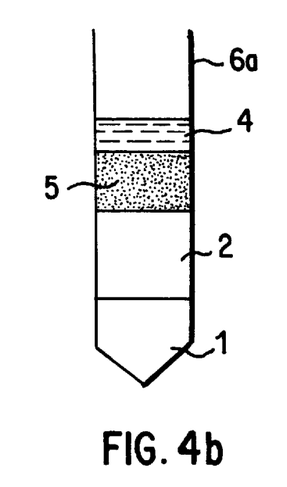

FIG. 4a [before centrifugation] and FIG. 4b [after centrifugation according to step (3°)] relate to a gelled system 10 according to the invention which is analogous to that of FIG. 3 but also comprises a layer of oil (paraffin oil), namely the protection phase 4, in a conical-bottomed centrifuge tube 6a. The development phase 1 is poured into the tube 6a, followed by the absorption phase 2 and then the protection phase 4, and said gelled system 10 is compressed by centrifugation (1000–3000 g for 10–20 minutes). The liquid sample 5 to be tested is then poured into the tube 6a. Said liquid sample 5 spreads out on top of the protection phase 4 (cf FIG. 4a).

During the centrifugation of step (3°), the liquid sample 5 migrates through the protection phase 4 and the solid particles it contains also migrate through the absorption phase 2 and/or the development phase 1 according to their size; on the other hand, the liquid of said liquid sample 5 and the ingredients dissolved therein do not pass through the absorption phase 2. After centrifugation, the largest and heaviest particles are spread out at the bottom of the tube 6a as indicated above.

Figure 5:
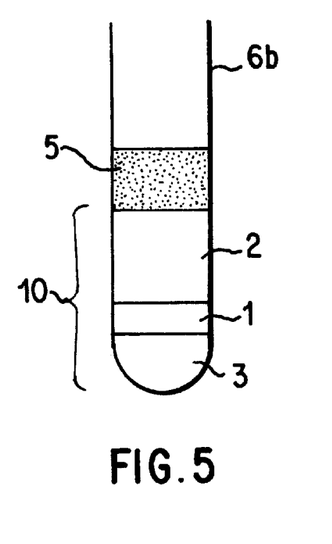
FIG. 5 shows a centrifuge tube containing a gelled system consisting of three phases, namely, from bottom to top, the barrier phase, the development phase and the absorption phase.

FIG. 5 relates to a gelled system 10 according to the invention comprising three layers, namely, from bottom to top: the barrier phase 3, the development phase 1 and the absorption phase 2, the layer 1 being a gel, the layer 2 being either a gel or a particulate phase and the layer 3 being either a gel or a solid paraffin.

The barrier phase 3 (melted beforehand if it consists of a paraffin which is solid at a temperature between RT and 50–55° C., and then cooled), the development phase 1 and then the absorption phase 2 are poured successively into a spherical-bottomed tube 6b. Said gelled system 10 is compressed by centrifugation (1000–3000 g for 10–20 minutes). The liquid sample 5 to be tested is then poured into the tube 6b. Said liquid sample 5 spreads out on top of the absorption phase 2 before the centrifugation of step (3°).

During the centrifugation of step (3°), the liquid of said liquid sample 5 and the dissolved constituents it contains do not migrate through the absorption phase 2; only the solid particles of said liquid sample 5 migrate, according to their size, through the gelled system 10 consisting of the combined absorption phase/development phase/barrier phase. When the barrier phase 3 is a solid paraffin, all the large and heavy particles do not pass through its thickness but spread out at the development phase/barrier phase interface according to their size.

The configuration of the layers 2, 1 and 3 according to FIG. 5 (the same applies to the gelled system of FIGS. 6a and 6b) offers the advantage of being able to reduce the thickness of the development phase 1 sandwiched between the absorption phase 2 and the barrier phase 3, and thus of improving the reading of the variation in OM, either with the naked eye (color change) or by means of a colorimeter.

Figure 6A:
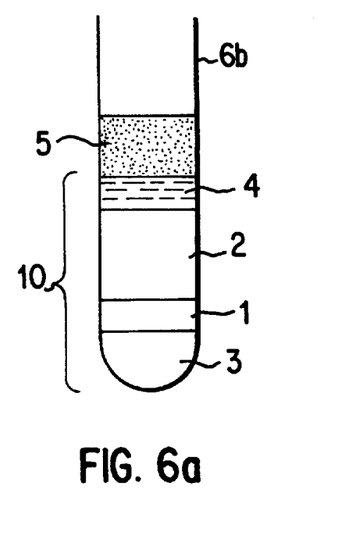
FIGS. 6a and 6b show a gelled system analogous to that of FIG. 5 which also contains the protection phase, as it appears before centrifugation (FIG. 6a) and after centrifugation (FIG. 6b)
Figure 6B:
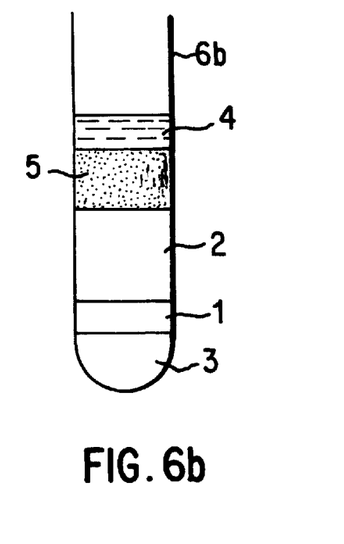

FIG. 6a [before the centrifugation of step (3°)] and FIG. 6b [after the centrifugation of step (3°)] relate to a gelled system 10 according to the invention which is analogous to that of FIG. 5 but also comprises a layer of oil 4 (paraffin oil) constituting the protection phase. The solid particles of the liquid sample 5 spread out as indicated for FIG. 5, the protection phase 4 enabling said liquid sample 5 to migrate during the centrifugation of step (3°).

The polymeric substances used in the swollen state in the gels (from top to bottom) of the absorption phase 2, the development phase 1 and the barrier phase 3 are advantageously dextran particles. Particularly suitable products are those of the Sephadex® G range marketed by PHARMACIA FINE CHEMICALS (Uppsala, Sweden), namely:

for the absorption phase 2, the product G 25C, for the development phase 1, the products G 25 to G 100 of so-called coarse to medium particle size, such as G 25M, G 50C, G 50M, G75 and G 100 (the preferred product being G 100), for the barrier phase 3, the products G 150 to G 200 of so-called medium to superfine particle size, such as G 150, G 150S, G 200 and G 200S (the preferred products being G 200 and especially G 200S).

The characteristics of these products of the dextran type are collated in Table I below.

TABLE I

| Phase | Gel | (A) | Fractionation range (MW) (B) | (C) |
|---|---|---|---|---|
| Absorption | G 25C | 100–300 | 1000–5000 | 100–5000 |
| Development | G 25M | 50–150 | 1500–30000 | 500–10000 |
|  | G 50C | 100–300 | 1500–30000 | 500–1000 |
|  | G 50M | 50–150 | 1500–30000 | 500–10000 |
|  | G 75 | 40–120 | 3000–80000 | 1000–50000 |
|  | G 100 | 40–120 | 4000–150000 | 1000–100000 |
| Barrier | G 150 | 40–120 | 5000–300000 | 1000–150000 |
|  | G 150S | 10–40 | 5000–150000 | 1000–150000 |
|  | G 200 | 40–120 | 5000–600000 | 1000–200000 |
|  | G 200S | 10–40 | 5000–250000 | 1000–200000 |

Notes:
(A): diameter in $\mu$m of the particles in the dry state
(B): globular peptides and proteins
(C): dextrans

TABLE I-continued

| | | Fractionation range (MW) | | |
|---|---|---|---|---|
| Phase | Gel | (A) | (B) | (C) |

G 25C: "Sephadex ® G 25 Coarse"
G 25M: "Sephadex ® G 25 Medium"
G 50C: "Sephadex ® G 50 Coarse"
G 50M: "Sephadex ® G 50 Medium"
G 75: "Sephadex ® G 75"
G 100: "Sephadex ® G 100"
G 150: "Sephadex ® G 150"
G 150S: "Sephadex ® G 150 Superfine"
G 200: "Sephadex ® G 200"
G 200S: "Sephadex ® G 200 Superfine"

The characteristics relating to the particle size in the swollen state and to the concentration, which are important according to the invention, have been given for the preferred gels in Tables II and III below.

TABLE II

| | | Diameter of the particles ($\mu$m) in the swollen state | |
|---|---|---|---|
| Phase | Gel | (A) | (B) |
| Absorption | G 25C | 160–530 | 172–516 |
| Development | G 100 | 90–320 | 103–311 |
| Barrier | G 200S | 30–130 | 32–129 |

Notes:
(A): range of the invention
(B); preferred range

TABLE III

| | | Concentration (g/ml) | | |
|---|---|---|---|---|
| Phase | Gel | (A) | (B) | (C) |
| Absorption | G 25C | 0.2 | 0.35 | 1 |
| Development | G 100 | 0.05 | 0.1 | 0.2 |
| Barrier | G 200S | 0.04 | 0.14 | 0.2 |

Notes:
(A): minimum concentration according to the invention
(B): preferred concentration according to the invention
(C): maximum concentration according to the invention The following comments should be made with reference to the minimum and maximum concentrations of the gels shown in Table III:

(1) if the gel in contact with the liquid of the liquid sample 5 (i.e. layer 1 of FIG. 1 or layer 2 of FIGS. 3 and 5) is more concentrated, there is a risk that said liquid sample 5 will pass through said gel during centrifugation;

(2) if all the gels are more concentrated, this seriously interferes with the detection of the presence or absence of microorganisms;

(3) if at least one of the gels is more dilute, exchanges of liquid can take place on the one hand between the liquid sample and the underlying gel, or on the other hand between two adjacent gels, thereby falsifying said detection.

It is possible to omit the barrier phase 3, as illustrated in FIGS. 1, 2a–2b, 3 and 4a–4b, when the large particles (erythrocytes, leukocytes, other cells) have no activity on the reagent which induces a detectable variation in optical measurement. This is particularly the case when said reagent is resazurin.

It is possible to omit the absorption phase 2 and the barrier phase 3, as illustrated in FIGS. 1 and 2a–2b, when no substance (dissolved or particulate) present in the liquid sample 5 has any activity on said reagent which induces a detectable variation in optical measurement, or when any possible interference can be inhibited during the development of step (4°).

If the concentration of the microorganisms which may be present in the liquid sample 5 to be tested, and which have migrated during the centrifugation of step (3°) to end up in the development phase 1 (either in the thickness of said phase 1 or on top of the interface between phase 1 and phase 3 or between phase 1 and the lower wall of the tube 6a), is above the detection threshold of the reagent of the development phase 1 which induces a detectable variation in optical measurement, the multiplication of the microorganisms by culture in situ in step (4°) is not necessary.

On the other hand, if after said centrifugation the concentration of the microorganisms is below the detection threshold, it is necessary to carry out said multiplication by culture in situ in said development phase 1 in the centrifuge tube, preferably at a temperature of 37° C.

The centrifuge tube 6a, 6b or 6c is made of a transparent material (plastic or glass). The centrifuge tube which can be used according to the invention will preferably be made of plastic and produced by molding. In a modified embodiment, said tube can be transparent over at least part of its peripheral surface, at the level of the zone packed with the development phase 1.

According to the invention, the detection threshold of the microorganisms, based on the initial concentration of said microorganisms in said liquid sample 5, is $10^3$ germs/ml, i.e. markedly lower than the threshold of $10^5$ germs/ml of the techniques of the prior art, illustrated especially by the above-mentioned Bac-T-Screen® and FiltraCheck®-UTI tests.

This improvement is due to the fact that, according to the invention, ($\alpha$) the microorganisms of the liquid sample 5 which have migrated during centrifugation are concentrated in the development phase 1, and then ($\beta$) if appropriate, they are multiplied in the nutrient medium.

To concentrate the microorganisms in the development phase, it is recommended according to the invention to use a development phase 1 with the smallest possible volume and thickness. The shape of the centrifuge tube will consequently be chosen so as to maximize the concentration factor of the microorganisms, which is directly proportional to the ratio of the volume of the test sample to the volume of the development phase. The volume of the development phase is determined by the formula $V=\pi R^2 h$ (where V is expressed in ml and the radius R and height h are expressed in cm). The smaller the diameter of the tube, the more the concentration factor increases. By way of example, the concentration factor can be a multiple of $10^3$ when the radius of the tube is divided by 10.

The capillary of the tube 6c allows a good concentration of the microorganisms in the development phase.

Figure 7:
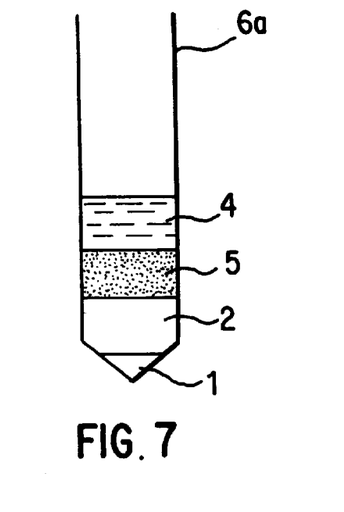
FIGS. 7 and 8 each show a preferred gelled system according to the invention, in which the development phase has a small thickness.
Figure 8:
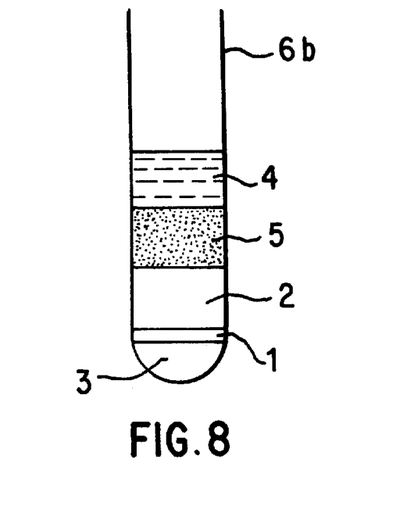

FIGS. 7 and 8 show preferred gelled systems according to the invention, as they appear after centrifugation. The tube of FIG. 7, which has similar contents to the tube of FIG. 4b, comprises a development phase 1 whose volume is smaller than those of the phase 2 and the sample 5 and which is accommodated at the bottom of said centrifuge tube 6a in the lower portion of the conical part.

The tube 6b of FIG. 8, which has similar contents to the tube of FIG. 6b, has a spherical bottom (whose diameter can be smaller than that of the rest of the tube) accommodating the barrier phase 3 and the development phase 1. This bottom is such that the development phase 1 sandwiched between the lower barrier phase 3 and the upper absorption phase 2 has the smallest possible volume and thickness.

By way of example, if a transparent plastic tube according to FIG. 8 is used which has a volume of 12 ml and an internal diameter of 1.35 cm and into which a volume of 6 ml of urine sample to be tested is introduced, to obtain the development phase 1 in the form of a 0.2 cm high ring, the volume of said phase 1 to be used must have a value V of $\pi.(1.35/2)^2.0.2$, i.e. about 0.3 ml. The concentration factor (F) of the microorganisms in the urine is then 6/0.3=20 for a colored ring to be visible. As the positive reaction starts with a spot representing less than a tenth of the diameter of the tube, the useful reaction volume of the development phase 1 then becomes 0.003 ml, which leads to a concentration factor of 6/0.003=2000, i.e. the sensitivity threshold of the concentration factor increases by a multiple of $10^3$, as mentioned above. In a modified embodiment, when the cross-section of the lower part of the tube is reduced by a factor of 10 (i.e. divided by 10 to give a diameter of 0.135 cm), V becomes $0.3 \times 10^{-2}$ ml, i.e. the factor F increases by $10^2$ for a ring and by $10^3$ for a spot.

Figure 9:
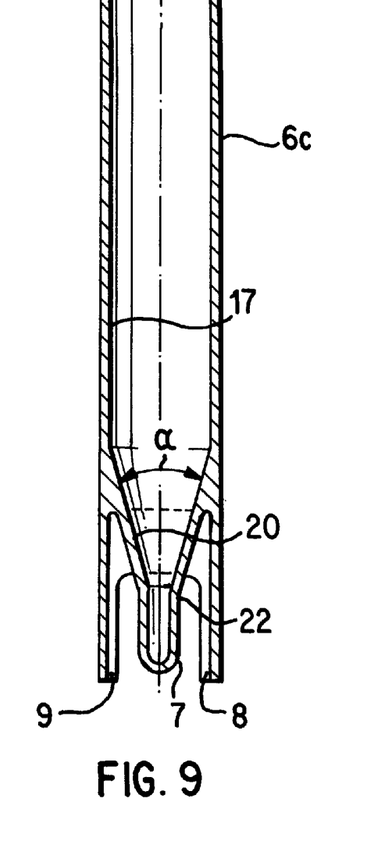
FIG. 9 shows a cutaway of a centrifuge tube according to the invention, provided with a capillary at the bottom.
Figure 10:
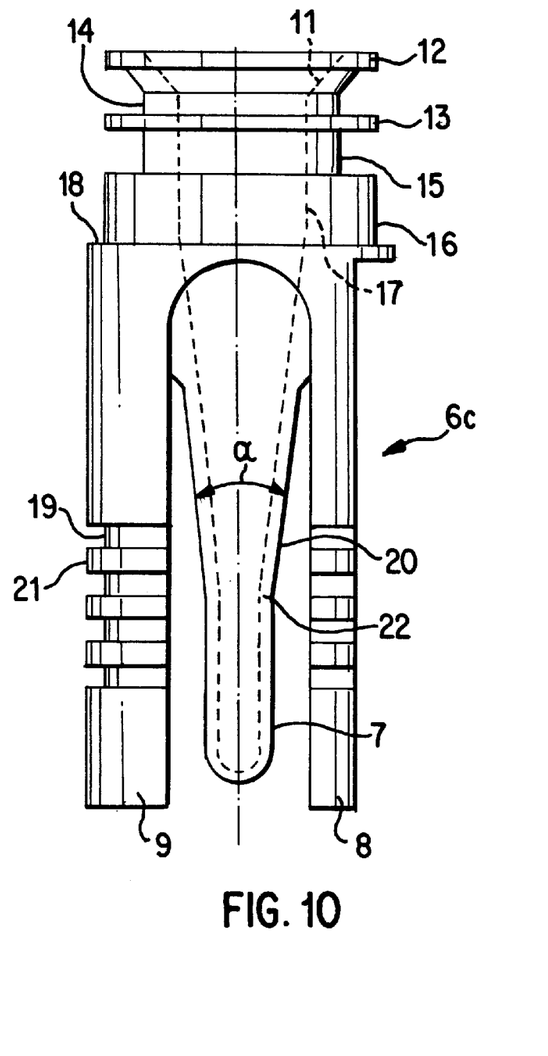
FIG. 10 shows a front view of another centrifuge tube according to the invention, which is also provided with a capillary.

FIGS. 9 and 10 each show a centrifuge tube 6c made of a transparent plastic (for example polystyrene or polycarbonate), which can be used according to the invention. The tube 6c offers the advantage that the microorganisms present in the development phase accommodated in the capillary can be counted.

According to FIG. 9, the tube 6c is provided at its lower end with a capillary 7 located along the axis of said tube, said capillary being intended to receive the development phase (reference 1 above). The cylindrical part of the tube 6c is joined to the mouth of the capillary 7 via a frustoconical portion 20. The development phase is accommodated in the capillary tube up to the line 22, which corresponds to the intersection of the frustoconical portion 20 with the mouth of the capillary 7. If appropriate, the protection phase (reference 4 above) and/or the absorption phase (reference 2 above) are accommodated above the line 22. The outer cylindrical wall of the tube 6c extends downwards, facing the capillary, in the form of two legs (or extensions) 8 and 9, which are approximately diametrically opposite one another and provide the tube with stability when it is upright. These legs 8 and 9 form a base; two windows are created between them and enable the contents of the capillary 7 to be observed with the naked eye or by means of an optical device (colorimeter, spectrometer, etc.), before centrifugation and then after centrifugation or culture, so that the bacteria or yeasts present can be counted.

The tube 6c of FIG. 10 is made on the one hand so that the bacteria or yeasts present can be counted, as indicated above for the tube of FIG. 9, and on the other hand so that said bacteria or yeasts present can be collected for identification. This tube comprises a capillary 7, a frustoconical wall 20 and an inner cylindrical wall 17, the line 22 corresponding to the intersection of the surface 20 with the mouth of the capillary 7. The mouth of the cylindrical portion 17 is either parallel to the axis of the tube 6c or, as shown by 11, funnel-shaped.

In the vicinity of the upper end, the outer surface of the tube 6c of FIG. 10 has one or more grooves 14 and/or 15 capable of accommodating an O-ring seal (especially made of rubber) not shown here, one of these grooves, 14, being located between two flanges or lips 12 and 13 and the other groove, 15, being located between the flange 13 and the outer surface 16 of the tube. An annular abutment 18 is provided on said outer surface 16. The assembly comprising the flange 12 and/or 13 and the outer surface 16 is intended to be sealed with a cylindrical cap, especially a plastic cap, covering the outer upper part of the tube 6c as far as the abutment 18. The legs or extensions 8 and 9 act as a base for keeping the centrifuge tube 6c upright, as indicated above for the tube of FIG. 9. A portion of the outward facing surface of one of these legs, 8, can be flat so that information can be written or stuck on said leg if appropriate. The legs 8 and 9 can also have a set of several alternating grooves 19 and lips 21 on their outward facing surface so that, if necessary, the tube 6c of FIG. 10 (which can have a very small height, in particular 30 mm) can be housed in the mouth of another (larger) centrifuge tube suitable for the centrifugation device used.

The bacteria or yeast present in the development phase accommodated in the capillary 7 up to the height of the line 22 are observed and counted by means of the windows created between the legs 8 and 9, as indicated above for the tube of FIG. 9.

To collect the microorganisms present in the development phase accommodated in the capillary 7 of the tube of FIG. 10, (1°) said tube is inverted to discard the supernatant, said development phase remaining in the capillary, (2°) an O-ring seal is placed in the groove 14, (3°) the assembly comprising the flange 12, the seal housed in the groove 14, the flange 13 and the surface 16 is inserted inside the mouth of a second centrifuge tube, containing the liquid recovery medium, until the second centrifuge tube comes into contact with the abutment 18, the tube 6c being kept upside down (i.e. with the capillary 7 pointing upwards), (4°) the two centrifuge tubes joined together in this way by their mouths are shaken, and then (5°) they are centrifuged at 1000–2000 g for 2–5 minutes to transfer the development phase, initially contained in the capillary 7, into the recovery liquid, which is at the bottom of the second tube.

This procedure enables the microorganisms present to be recovered easily, without contamination and substantially without loss. This technique is much more efficient than that which consists in removing the development phase accommodated in the capillary 7 by means of suction with a syringe; in fact, the swollen polymer particles of the gel constituting the development phase do not easily pass through the syringe needle because of their dimensions.

In a modified embodiment, the bulk of the development phase containing microorganisms can be collected by using the tube of FIG. 9. To do this, (1a) the supernatant situated above the line 22 is discarded, (2a) an aqueous washing solution is added and the tube 6c is sealed and shaken, (3a) the tube is centrifuged at 1000–2000 g for 2–5 minutes, (4a) operations (2a) and (3a) are repeated until the supernatant is colorless, and (5a) the resulting supernatant is discarded, an aqueous recovery solution is added and the tube is shaken to collect the resulting liquid medium containing the bulk of the development phase and hence most of the microorganisms present.

From a practical point of view, so that the development phase remains in the capillary when the tube 6c is inverted before shaking and then centrifugation, it is important for the internal diameter of the capillary to be less than or equal to 2.5 mm. An appropriate internal diameter is between 1.2 and 2.3 mm. Very good results have been obtained with internal diameters of 2.0 and 2.2 mm.

To improve the sensitivity of the detection of the microorganisms and achieve a good recovery of the development phase, it is recommended to satisfy at least one, and preferably all, of the following conditions:

A- the internal diameter of the capillary is less than 2.5 mm,

B- the angle $\alpha$ of the frustoconical portion 20 is less than or equal to 30° (i.e. $\leq \pi/6$), that is to say that the generatrix of this frustoconical portion is slightly inclined relative to the vertical axis of the tube (angle of inclination less than or equal to $\alpha/2$), C- the volume of the capillary is less than or equal to 0.6 ml and preferably less than or equal to 0.1 ml.

If condition B or condition C is not satisfied, there is a risk that traces of development phase, and hence microorganisms, may be deposited on the inner wall of the tube, especially above the region of the intersection 22.

EXAMPLE 1

The following are introduced successively into a transparent plastic centrifuge tube with a volume of 5 ml and an internal diameter of 1.10 cm:

0.5 ml of a gel of G 200S/distilled water, in which the G 200S has a concentration by dry weight of 0.2 g/ml and a particle size in the swollen state of 40–100 μm, to form the barrier phase;

0.25 ml of a gel of G 100/aqueous culture medium, in which the G 100 has a concentration by dry weight of 0.2 g/ml and a particle size in the swollen state of 120–300 μm, said aqueous culture medium having the following composition:

| heart-brain broth | 37 g/l |
|---|---|
| glucose | 5 g/l |
| agar (type IX) | 0.33 g/l |
| pH | 7.4 ± 0.1 | and containing 0.05 g/ml of resazurin, to form the development phase; and 0.5 ml of a gel of G 25C/distilled water, in which the G 25C has a concentration by dry weight of 1 g/ml and a particle size in the swollen state of 40–110 μm, to form the absorption phase.

The resulting gelled system is compressed by centrifugation (1000–3000 g for 10–20 minutes at RT). In a modified embodiment, said compressing centrifugation can be carried out after the introduction of each of said phases and before the introduction of the next phase.

The gelled system obtained by this process is ready to use.

EXAMPLE 2

1 ml of paraffin oil is introduced as a protection phase on top of the gelled system prepared according to Example 1 above.

This gives a device for detecting the presence or absence of microorganisms in a sample of a biological material, said device being stable on storage.

EXAMPLE 3

The following are introduced successively into a transparent plastic centrifuge tube with a volume of 5 ml and an internal diameter of 1.10 cm:

0.5 ml of a paraffin melting at a temperature above or equal to 50° C. (this paraffin being introduced in the molten state), to form the barrier phase (after cooling to RT);

0.25 ml of a gel of G 100/aqueous culture medium, in which the G 100 has a concentration by dry weight of 0.2 g/ml and a particle size in the swollen state of 103–311 μm, said aqueous culture medium having the following composition:

| heart-brain broth | 37 g/l |
|---|---|
| glucose | 5 g/l |
| agar (type IX) | 0.33 g/l |
| pH | 7.4 ± 0.1 | and containing 2 mmol/l of H-L-Ala-NA in phosphate buffer (0.1 M) at pH 8.0, to form the development phase; and 0.5 ml of a gel of G 25C/distilled water, in which the G 25C has a concentration by dry weight of 1 g/ml and a particle size in the swollen state of 32–129 μm, the distilled water used to produce this gel containing 0.06 g/ml of EDTA, to form the absorption phase.

The resulting gelled system is compressed by centrifugation (1000–3000 g for 10–20 minutes at RT). In a modified embodiment, said compressing centrifugation can be carried out after the introduction of each of said phases and before the introduction of the next phase.

The gelled system obtained by this process is ready to use.

EXAMPLE 4

0.25 ml of paraffin oil is introduced as a protection phase on top of the gelled system prepared according to Example 3 above.

This gives a device for detecting the presence or absence of microorganisms in a sample of a biological material, said device being stable on storage.

EXAMPLE 5

The procedure is as indicated in Example 3 except that the aqueous culture medium used for swelling the G 100 to obtain the development phase also contains the diazotization reagent p-dimethylaminocinnamaldehyde.

EXAMPLE 6

The following are introduced successively into a conical-bottomed transparent plastic centrifuge tube with an internal diameter (in its cylindrical portion) of 1 cm and a volume of 5 ml:

0.20 ml of a gel of G 100/aqueous culture medium, in which the G 100 has a concentration by dry weight of 0.2 g/ml and a particle size in the swollen state of 103–311 μm, said aqueous culture medium having the following composition:

| YNB | 6.7 g/l |
|---|---|
| maltose | 20.0 g/l |
| gentamycin | 0.05 g/l |
| cycloheximide | 0.5 g/l |
| pH | 6.0 | and containing 1 mmol/l of H-L-Pro-pNA (this culture medium containing a substrate specific for strains of *Candida albicans* so that said *Candida albicans* can be distinguished from the other Candida), to form the development phase; and 0.5 ml of micronized kaolin with a homogeneous particle size of 0.055–0.060 μm, to form the absorption phase.

The resulting gelled system is compressed by centrifugation at 2000 g for 15 minutes at RT.

The gelled system obtained by this process is ready to use and is intended specifically for the identification of *Candida albicans* among a group of non-isolated strains of Candida.

EXAMPLE 7

1 ml of paraffin oil is introduced on top of the gelled system prepared according to Example 6 in order to form the protection phase, and the resulting gelled system is compressed by centrifugation at 2000 g for 15 minutes at RT.

EXAMPLES 8 and 9

The procedure is as indicated in Example 6 above except that 0.20 ml of the nutrient medium of Example 1, containing resazurin, is used as the nutrient medium to obtain the development phase for the preparation of a gelled system specific for the detection of bacteria (Example 8). The resulting gelled system is used to prepare, according to Example 7, a ready-to-use gelled system comprising the protection phase (Example 9).

EXAMPLES 10 and 11

The procedure is as indicated in Example 6 above except that 0.20 ml of a nutrient medium specific for strains of Aspergillus is used as the nutrient medium to obtain the development phase for the preparation of a gelled system specific for the detection of these yeasts (Example 10). The resulting gelled system is used to prepare, according to Example 7, a ready-to-use gelled system comprising the protection phase (Example 11).

EXAMPLE 12

A volume of 1 to 4 ml of sterilized urine (into which different concentrations of strains of *Escherichia coi* had been introduced), or of urine from a patient suffering from a urinary infection caused by strains of *Escherichia coli*, was introduced into the tubes containing the gelled systems prepared according to Examples 1 and 5. After centrifugation at 3000–5000 g for 20 minutes at RT in the case of an infected urine sample containing strains of *Escheridia coli* at a concentration of $10^5$ CFU/ml, a pink spot is observed with resazurin (i.e. the gelled system prepared according to Example 1) and a red spot is observed with the mixture H-L-Ala-NA/diazotization reagent (i.e. the gelled system prepared according to Example 5). These colored spots located in the development phase spread and each form a colored ring after a few hours at RT or 37° C.

The results obtained with resazurin have been collated in Table IV below.

TABLE IV

Detection of strains of *Escherichia coli* with resazurin

| Reading | Bacteria/ml in infected urine | | | | | |
|---|---|---|---|---|---|---|
| | $10^8$ | $10^7$ | $10^6$ | $10^5$ | $\leq 10^4$ | $10^3$ |
| at t = 0.5 h | +++ | +++ | +++ | ++ | + | +/− |
| at t = 2 h | +++ | +++ | +++ | +++ | +++ | +++ |

EXAMPLE 13

Complementary tests were performed on batches of urine taken from 50 people (35 people suffering from a bacterial urinary infection and 15 people, used as controls, not suffering from a urinary infection). The gelled systems of Examples 1–5 were used simultaneously for each urine sample tested. 2 ml of urine were introduced into each of the centrifuge tubes.

After centrifugation at 3000–5000 g for 15 minutes at RT, followed by culture in situ at 37° C. for 24 h, the Sen, Spe and NPV (for low bacterial concentrations) observed with these urine samples were improved when using the gelled systems according to the invention, compared with the above-mentioned Bac-T-Screen® and FiltraCheck®-UTI tests. Some of the results obtained are collated below for a concentration of $10^3$ bacteria/ml in the urine samples:

Sen=95–98%

Spe=93–97%

NPV=91–94%

EXAMPLE 14

The gelled system of Example 2 was used to assess the presence or absence of bacteria in 8 operating theater suites. The tubes (with a volume of 15 ml), packed with said gelled system and optionally provided with a flange of the funnel type at their upper orifice, were placed in operating theater suites for 24 h in the vicinity of the gas inlets, at a height of 1.50 m and at a distance of 1 m from the nearest wall. Distilled water was run over the tubes from a pipette in order to rinse the exposed part of each tube and of each flange present. After centrifugation (30 minutes at 3000 g) and culture in situ at 37° C. for 24 h, it was possible to detect the presence of bacteria (mainly strains of Staphylococcus) in the ambient atmosphere of one of the operating theater suites. The contaminated operating theater suite was sterilized.

EXAMPLE 15

The filters (cellulose membranes) of the ventilation ducts of 6 operating theater suites were cut up and then finely dilacerated. The material obtained was triturated with distilled water; the resulting supernatant was introduced at a rate of 1 to 2 ml into tubes obtained by the process of Examples 2 and 11. After centrifugation at 3000–5000 g for 15 minutes at RT, followed by culture in situ at 37° C. for 24 h, it was possible to detect the presence of bacteria (mainly strains of Pseudomonas) in one of the six operating theater suites and the presence of yeasts (strains of Aspergillus in this instance) in another of said operating theater suites. The two contaminated operating theater suites were sterilized.

EXAMPLE 16

"Clarified" (i.e. delipidated) and sterilized milk was contaminated with strains of Candida (at a concentration greater than or equal to $10^5$ germs/ml) and distributed at a rate of 2.5 ml into batches of centrifuge tubes (5 tubes per batch) prepared by the process of Example 7:

batch A containing isolated strains of *Candida albicans*, batch B containing isolated strains of *Candida glabrata*, batch C containing isolated strains of *Candida krusei*, batch D containing non-isolated strains of various Candida (i.e. strains of *Candida albicans* associated with other strains of Candida), and the control batch consisting of said clarified and sterilized milk.

After centrifugation at 3500–4000 g for 20 minutes at RT, followed by culture in situ at 37° C. for 1–2 h, it was found that the gelled system of Example 7 gave a positive color reaction with the tubes of batches A and D and did not give a positive color reaction with batches B and C and the control batch.

EXAMPLE 17

A hemoculture sample (taken from an infected patient) which has been brought into contact beforehand with saponin (to lyze the erythrocytes present) is introduced at a rate of 1 to 3 ml into a centrifuge tube packed with the gelled system prepared by the process of Example 4. The tube is centrifuged at 3000–5000 g for 15 minutes at RT. After culture in situ at 37° C. for 1–2 h, a positive color reaction is observed in said centrifuge tube, indicating the presence of Gram-negative bacteria in the hemoculture.

In a modified embodiment, by introducing an antibiotic into the development phase or into the combined development phase/absorption phase so as to have a set of several tubes each containing a different antibiotic, it is possible to assess the resistance of the bacteria contained in hemocultures towards customary antibiotics.

EXAMPLE 18

Some beef is cut up and finely dilacerated. Isotonic solution and bacteria ($10^7$ germs/ml of strains of *Staphylo-*

*coccus epidermidis*) are added to the resulting material. The supernatant is collected and introduced at a rate of 1–2 ml into a tube containing the gelled system prepared by the process of Example 2.

The tube is centrifuged at 3000–5000 g for 15 minutes at RT culture in situ at 37° C. for 24 h. A color change is observed in the lower part of the development phase, confirming the presence of bacteria in the sample tested.

EXAMPLE 19

The following are introduced successively into a transparent plastic centrifuge tube with a height of 30 mm, which is provided with a capillary ($\Phi$=2.2 mm; volume=0.045 ml) and corresponds to FIG. 10, the tube being centrifuged after each introduction (1000–3000 g for 10–20 minutes at RT) in order to compress each layer:

0.045 ml of a gel of G 100/aqueous culture medium, in which the G 100 has a concentration by dry weight of 0.2 g/ml and a particle size in the swollen state of 103–311 $\mu$m, this medium containing resazurin, and 0.5 ml of paraffin oil.

A urine sample from a patient suffering from a urinary infection caused by strains of *Escherichia coli* is then introduced. After 20 minutes at 3000–5000 g at RT, the coloration of the characteristic of the presence of bacteria is observed 1 hour after centrifugation was begun.

The bacteria are counted optically (spectrometer, densitometer or MacFARLAND apparatus for measurement of the turbidimetry), if appropriate with standard urine solutions each containing a known amount of *Escherichia coli*.

The development phase is recovered, as explained above, by means of a second centrifuge tube containing the aqueous recovery solution. This is used to establish antibiograms for assessing the resistance of the bacteria collected towards several antibiotics.

Particularly effective results are obtained when the volume of the capillary 7 is reduced to 0.02–0.03 $\mu$l.

According to the invention, an assay kit is recommended which comprises at least (1) a conical-bottomed centrifuge tube 6a containing a gelled system consisting, from top to bottom, of the protection phase 4, the absorption phase 2 and the development phase 1, a spherical-bottomed centrifuge tube 6b containing a gelled system consisting, from top to bottom, of the protection phase 4, the absorption phase 2, the development phase and the barrier phase 3, or a capillary-bottomed centrifuge tube 6c containing a gelled system consisting of the development phase on which the protection layer and/or the combined protection layer+absorption layer rest, if appropriate; and/or (2) bottles containing the constituent materials (i.e. the gel or gels, the particulate substance, the solid paraffin and/or the liquid paraffin) of said phases, the reagent which induces a detectable variation in optical measurement in the presence of microorganisms and, if appropriate, the culture medium for the swelling of said development phase 1.

It is also recommended to use the method and the gelled system according to the invention for detecting the presence or absence of bacteria in a blood or urine sample, especially in the field of hemoculture screening and urine screening, identifying a strain of microorganism in a biological sample by using, in the development phase, ($\alpha$) a reagent which induces a detectable variation in optical measurement, and ($\beta$) a culture medium, both of which are specific for said strain, counting the microorganisms present in the development phase, collecting the development phase containing microorganisms for the purpose of studying the latter, or determining the resistance of strains of microorganisms towards a group of customary antibiotics.

We claim:

1. A method of detecting microorganisms selected from the group consisting of bacteria and yeasts in a liquid sample of a biological material, said method comprising:

(1) using a gel system which
  (i) separates, according to microorganism size, microorganisms in said liquid sample from other solid components,
  (ii) is essentially impermeable to water and dissolved substances, and
  (iii) comprises
    (a) a development phase gel including a microorganism culture medium and a reagent capable of inducing a detectable variation in optical measurement in the presence of microorganisms, and a first phase intimate mixture which comprises water originating wholly or partly from the culture medium and water-absorbing polymer particles so that, in said first phase intimate mixture, said polymer particles a) are in a concentration by dry weight to water of between 0.05 g/ml and 0.2 g/ml and b) have a diameter in a swollen state of between 90 and 320 $\mu$m, and
    (b) a protection phase which comprises an inert oil with a density less than that of water and wherein said protection phase rests on said development phase gel;

(2) placing said gel into a centrifuge tube and introducing said liquid sample to said centrifuge tube to be disposed on top of said gel;

(3) centrifuging the centrifuge tube; and (4) detecting microorganisms in said liquid sample by inducing a detectable variation in optical measurement in said reagent in the centrifuge tube, wherein after step 3, said protective phase rests on the water of said liquid sample.

2. The method of claim 1, wherein said liquid sample contains cells other than microorganisms.

3. The method of claim 1, wherein said protective phase is paraffin oil.

4. The method of claim 1, wherein said centrifugation step (3) is carried out at 1000–5000 g.

5. The method of claim 1, wherein step (4) is carried out after multiplication of the microorganisms in said culture medium at a temperature between room temperature and 45° C. for at most 24 hours for bacteria and for at most 36 hours for yeast.

6. The method of claim 5, wherein multiplication occurs for 1 to 2 hours for bacteria and 24 to 30 hours for yeast.

7. The method of claim 1, wherein the gel system further comprises:

an absorption phase essentially impermeable to water and substances dissolved therein which during centrifugation retains insoluble particles contained in said liquid sample which have a size less than 5 $\mu$m, but lets through particles with a size greater than or equal to 5 $\mu$m and which comprises (i) a gel or (ii) silica or silicate particles with a size less than 0.1 $\mu$m, wherein said absorption phase rests on said development phase and said protection phase rests on said absorption phase.

8. The method of claim 7, wherein said absorption phase is a gel consisting of a second intimate mixture of water and water-absorbing polymer particles so that, in said second phase intimate mixture, said polymer particles have a) a concentration by dry weight to water of between 0.2 g/ml and 1 g/ml and b) a diameter in the swollen state of between 160 μm and 530 μm.

9. The method of claim 7, wherein said absorption phase is a layer consisting of a mineral substance which is micronized so as to have a particle size less than 0.1 μm in the dry state and does not essentially swell in the presence of water.

10. The method of claim 9, wherein said mineral substance is selected from the group consisting of silica and silicates.

11. The method of claim 10, wherein the mineral substance consists of kaolin.

12. The method of claim 7, wherein said absorption phase further comprises at least one substance which (i) inhibits contaminants, (ii) lyzes cells or (iii) eliminates lipids in said liquid sample originating from said biological material.

13. The method of claim 7, wherein said absorption phase further comprises at least one substance which (i) inhibits contaminants, (ii) lyzes cells and (iii) eliminates lipids in said liquid sample originating from said biological material.

14. The method of claim 12, wherein said substance interferes with said contaminants, cells or lipids from reacting with said reagent in step (4).

15. The method of claim 7, wherein in step (1), said gel system further comprises:
a barrier phase which comprises a phase that cannot be crossed during step (3) by any microorganisms present, said barrier phase being located underneath said development phase so that said development phase rests on said barrier phase.

16. The method of claim 15, wherein barrier phase consists of a solid paraffin melting at a temperature above the multiplication temperature of the microorganisms.

17. The method of claim 15, wherein said barrier phase is a gel consisting of a third phase intimate mixture of water and water-absorbing polymer particles so that, in said third phase intimate mixture, said polymer particles have a) a concentration by dry weight of between 0.04 g/ml and 0.2 g/ml and b) a diameter in the swollen state of between 30 μm and 130 μm.

18. The method of claim 15, wherein one of the following is used in step (1):
(i) a gel system comprising, from top to bottom, in a conical-bottomed centrifuge tube:
said protective phase,
said absorption phase and
said development phase;
(ii) a gel system comprising, from top to bottom, in a round-bottomed or spherical-bottomed centrifuge tube:
said protective phase,
said absorption phase,
said development phase and
said barrier phase; or
(iii) a gel system comprising, from top to bottom, in a centrifuge tube with a capillary provided at a bottom of said centrifuge tube:
said protective phase,
said absorption phase and
said development phase.

19. The method of claim 18, wherein the volume of said development phase is smaller than the volume of said absorption phase and said liquid sample combined in order to concentrate the microorganisms during centrifugation.

20. A method of use selected from the group consisting of:
a) detecting bacteria in a blood or urine sample,
b) identifying a strain of microorganism in a biological sample using (i) a reagent which induces a detectable variation in optical measurement, and (ii) a culture medium, said reagent and said culture medium being specific for said strain,
c) counting microorganisms,
d) collecting microorganisms for study, and
e) determining resistance of strains of microorganisms towards a group of antibiotics, comprising the steps of the method of claim 1.

21. The method of claim 20, wherein said detection in a blood or urine sample occurs in hemoculture screening and urine screening.

22. A gel system for detecting microorganisms in a centrifuge tube, said gel system comprising:
a development phase comprising a gel containing microorganism culture medium and a reagent capable of inducing a detectable variation in optical measurement in the presence of microorganisms and a first phase intimate mixture which comprises water originating wholly or partly from the culture medium and water-absorbing polymer particles so that, in said first phase intimate mixture, said polymer particles have a) a concentration by dry weight of between 0.05 g/ml and 0.2 g/ml and b) a diameter in a swollen state of between 90 μm and 320 μm; and
a protection phase which is an inert oil with a density less than that of water and wherein said protective phase rests on said development phase.

23. The gel system of claim 22, wherein said inert oil is paraffin oil.

24. The gel system of claim 22, further comprising:
an absorption phase essentially impermeable to water and substances dissolved therein, said absorption phase during centrifugation retaining the insoluble particles contained in said liquid sample which have a size less than 5 μm but letting through particles with a size greater than or equal to 5 μm, said absorption phase comprising (i) a gel or (ii) silica or silicate particles with a size less than 0.1 μm, said absorption phase rests on said development phase and said protection phase rests on said absorption phase.

25. The gel system of claim 24, wherein said absorption phase is a gel consisting of a second phase intimate mixture of water and water-absorbing polymer particles so that, in said second phase intimate mixture, said polymer particles have a) a concentration by dry weight to water of between 0.2 g/ml and 1 g/ml and b) a diameter in a swollen state of between 160 μm and 530 μm.

26. The gel system of claim 24, wherein said absorption phase is a layer consisting of a mineral substance which is micronized so as to have a particle size less than 0.1 μm in the dry state and does not essentially swell in the presence of water.

27. The gel system of claim 24, further comprising:
a barrier phase which cannot be crossed after centrifugation by any microorganisms present, said barrier phase being located underneath the development phase so that said development phase rests on said barrier phase.

28. The gel system of claim 27, wherein said barrier phase consists of a solid paraffin melting at a temperature above the multiplication temperature of the microorganisms.

29. The gel system of claim 27, wherein said barrier phase is a gel consisting of a third phase intimate mixture of water and water-absorbing polymer particles so that, in said third phase intimate mixture, said polymer particles have a) a concentration by dry weight to water of between 0.04 g/ml and 0.2 g/ml and b) a diameter in a swollen state of between 30 μm and 130 μm.

30. A gel system for detecting microorganisms in a centrifuge tube, said gel system comprising:

a development phase comprising a gel containing microorganism culture medium and a reagent capable of inducing a detectable variation in optical measurement in the presence of microorganisms and a first phase intimate mixture which comprises water originating wholly or partly from the culture medium and water-absorbing polymer particles so that, in said first phase intimate mixture, said polymer particles have a) a concentration by dry weight of between 0.05 g/ml and 0.2 g/ml and b) a diameter in a swollen state of between 90 $\mu$m and 320 $\mu$m.

31. The gel system of claim 30, further comprising:

a protection phase which is an inert oil with a density less than that of water and wherein said protective phase rests on said development phase.

* * * * *